(12) United States Patent
Surridge

(10) Patent No.: US 6,301,329 B1
(45) Date of Patent: Oct. 9, 2001

(54) TREATMENT PLANNING METHOD AND APPARATUS FOR RADIATION THERAPY

(75) Inventor: Michael Surridge, Southampton (GB)

(73) Assignee: The University of Southampton, Southampton (GB)

( * ) Notice: Subject to any disclaimer, the term of this patent is extended or adjusted under 35 U.S.C. 154(b) by 0 days.

(21) Appl. No.: 09/633,242

(22) Filed: Aug. 7, 2000

Related U.S. Application Data

(63) Continuation of application No. PCT/GB99/00403, filed on Feb. 9, 1999.

(30) Foreign Application Priority Data

Feb. 9, 1998 (GB) .................................................. 9802635
Dec. 11, 1998 (GB) .................................................. 9827379

(51) Int. Cl.$^7$ .................................................. A61N 5/10
(52) U.S. Cl. .................................................. 378/65; 702/179
(58) Field of Search .................................................. 378/65; 702/179

(56) References Cited

U.S. PATENT DOCUMENTS

| | | | |
|---|---|---|---|
| 4,455,609 | 6/1984 | Inamura et al. | 250/370.07 |
| 5,341,292 | 8/1994 | Zamenhof | 600/425 |
| 5,844,241 | * 12/1998 | Liu et al. | 250/363.04 |
| 5,870,697 | * 2/1999 | Chandler et al. | 702/179 |
| 6,029,079 | * 2/2000 | Cox et al. | 600/407 |
| 6,148,272 | * 11/2000 | Bergstrom et al. | 702/179 |
| 6,175,761 | * 1/2001 | Frandsen et al. | 600/436 |

FOREIGN PATENT DOCUMENTS

| | | |
|---|---|---|
| 90/14129 | 11/1990 | (WO) . |
| 91/18552 | 12/1991 | (WO) . |
| 95/20354 | 8/1995 | (WO) . |
| 97/32630 | 9/1997 | (WO) . |
| 97/42522 | 11/1997 | (WO) . |

OTHER PUBLICATIONS

King et al., "An Investigation Of The Filtering Of Tew Scatter Estimates Used To Compensate For Scatter With Ordered Subset Reconstruction", IEEE Transaction on Nuclear Science 44(3), 1140–1145 (1997).*
Bromda et al., "Application Hints For Savitzky–Golay Digital Smoothing Filters", Anal. Chem. 53, 1583–1586 (1981).
King et al., "An Investigation Of The Filtering Of Tew Scatter Estimates Used To Compensate For Scatter With Ordered Subset Reconstructions", 1996, pp. 1077–1081.
Turton, "A Novel Variant Of The Savitzky–Golay Filter For Spectroscopic Applications", Meas. Sci. Technol. 3, 858–863 (1992).
Gill et al., "RAPT: A Parallel Radiotherapy Treatment Planning Code", International Conference and Exhibition HPCN Europe 1996 Proceedings, pp. 183–189.

* cited by examiner

Primary Examiner—Robert H. Kim
Assistant Examiner—Allen C. Ho
(74) Attorney, Agent, or Firm—Renner, Otto, Boisselle & Sklar LLP

(57) ABSTRACT

A radiation modeling apparatus comprises; a storage means (350, 360) containing details of material properties of at least one medium (100, 105, 110) which may undergo irradiation and details of the properties of at least one radiation beam (45a, 45b, 45c) operable to irradiate the media; a stochastic modeling kernel (340) operable to receive parameters of an irradiation and calculate a distribution of radiation (380) resulting from the irradiation using data from the storage means (350, 360); characterized by a filter (370) arranged so as to remove components comprising substantially statistical noise from the output of the modeling kernel (340).

18 Claims, 9 Drawing Sheets

TREATMENT PLANNING METHOD AND APPARATUS FOR RADIATION THERAPY

This application is a continuation of International Application No. PCT/GB99/00403 filed Feb. 9, 1999, which is hereby incorporated herein by reference in its entirety".

This invention relates to radiation modelling apparatus and methods for radiation modelling.

It is often desirable to know to a good approximation the characteristics of a radiation beam. Such a beam may be emitted for treatment purposes from a linear accelerator or may represent leakage from a radioactive source. One application where the beam characteristics must be known in considerable detail is in radiotherapy treatment planning.

The purpose of radical radiotherapy treatment is to deliver a lethal dose of radiation to tumour cells while keeping the radiation dose delivered to normal cells as low as possible. To accomplish this several beams of radiation are aimed into a patient from a variety of different directions, as shown schematically in FIG. 1A of the accompanying drawings. Energy is deposited into tissue lying along the path of the beam and thus a much greater amount of energy is deposited in the region where all the beams overlap, as shown, for example, in the dose contours of FIG. 1B.

Radiotherapy treatment planning aims to ensure that this beam overlap region encompasses only tumour cells, and that a high amount of energy is deposited uniformly throughout the tumour region as a radiation dose. Radiotherapy treatment planning has other secondary aims. It is important to ensure that particularly radiosensitive tissues receive a dose lower than a threshold where permanent disability or debilitating side effects may occur, and that the total dose delivered be kept to a minimum. In FIG. 1A a schematic cross section of the skull of a radiotherapy patient receiving treatment is shown. The patient is lying on a treatment couch 30. The patient has a brain tumour 20 represented by an area enclosed by thick line 25. Geometrical edges of three radiation beams 45a, 45b and 45c used to treat the tumour 20 are shown being emitted from a linear accelerator treatment head 40 which is rotated around the centre of the tumour into three different positions 40a, 40b and 40c. These three positions 40a 40b and 40c, together with the width, length and relative weight of the beams are chosen to ensure an even dose distribution across the tumour and avoid radiosensitive areas like the patient's eyes 50. A high dose area 60 where all the radiation beams 45a 45b 45c overlap is indicated by hatching and is constructed to coincide with the tumour 20.

FIG. 1B shows a dose distribution predicted (by modelling) to be produced by the three radiation beams 45a 45b and 45c. Isodose lines 70 indicate the relative dose to different parts of the patient's brain. These isodose lines 70 vary depending on the properties of radiation beams 45a, 45b and 45c. They are used to determine whether the dose received by the tumour 20, the patient's normal tissue and the patient's eyes 50 is clinically acceptable. For example, according to well established clinical guidelines the dose across the tumour should be uniform to within ±5%. This is clearly not achieved in FIG. 1B. The plan shown in FIG. 1B would be refined, for example by changing the position, weighting and field widths of the radiation beams 45a, 45b and 45c, until this and other clinical objectives were met.

The amount of radiation to be received by the patient is prescribed with consideration of the treatment plan. If the treatment plan indicates that the dose to sensitive areas is too high shielding blocks will be used; if, on the other hand the dose to the skin is too low wax may be placed around the treatment site. It is, therefore, vital that the treatment plan is as accurate as reasonably possible. In order for the planner to try out treatment options the plan must also be complete within a reasonable period of tire, which is usually less than one hour. It is this compromise that the various types of treatment planning system address.

The difficulty of reconciling these clinical objectives is exacerbated as many types of tissue show damage from radiation only at a very late point in the treatment, when the dose that they may have received is already sufficient to cause necrosis and tissue failure. This is particularly true in the head and neck region where a high dose is needed for cure, but critical structures such as the spinal cord lie within or close to the high dose region. The delicate balance of chance of cure against the chance of late tissue necrosis is known as the therapeutic ratio and defined as "the ratio of probability of irradicating tumour within the irradiated volume to the probability of causing severe late damage to normal tissue".

The relationship between dose and normal tissue injury and tumour cure is shown schematically in FIG. 2 of the accompanying drawings. This graph shows the probability of an effect on the y axis versus the integral dose on the x axis. It may be seen that due to fractionation (dividing the treatment into many small sessions) and other radiobiological reasons the tumour cells are more susceptible to radiation than normal tissue—the curve 170 for tumour cells lies to the left of the curve 180 for normal tissue. Ideally a dose 200 is given such that there is a large probability 170 for tumour cure but a small probability 180 for normal tissue necrosis— i.e. a vertical line 190 drawn between the two curves is at a maximum. It may be seen that if the dose 200 is moved slightly to the left the probability of tumour cure drops rapidly while if it is moved slightly to the right the probability of normal tissue necrosis rises rapidly. A small error on the treatment plan could therefore greatly reduce the chance of cure or greatly increase the chance of normal tissue necrosis, and the resultant undesirable side effects such as blindness or paralysis.

Due to the increase in normal tissue necrosis the total dose delivered must be kept as low as possible. Physicians therefore generally prescribe the minimum dose to the tumour area that will achieve a high probability of killing the tumour. The dose variation across the tumour area depends on the characteristics of the beams and so an inaccurate model of beam characteristics may result in a false impression of uniformity across tumour volume in the treatment plan while in fact some areas are receiving less dose, enabling the tumour to survive. This may result in the death of the patient. On the other hand there may be areas of the patient which receive higher doses than indicated by the treatment plan, resulting in necrosis of the tissue and, for example, possible failure of the spinal cord. Any improvement, therefore in the modelling of beam characteristics that gives rise to a more accurate treatment plan could have significant clinical implications.

Beam characteristics vary with many different parameters. The dose profile of a radiation beam from a linear accelerator, for example, has more of a rectangular shape than that formed by a Cobalt 60 radiation source. Once the beam is formed it undergoes flattening, collimation and possibly shaping with wedges or multi-leaf collimators. The beam interacts with these devices, generating secondary scattered electrons which will influence the dose distribution in the patient. Such beam characteristics are highly individual, with even two machines of the same design generating beams with different characteristics.

Cancer affects many people, a significant proportion of whom will need radical radiotherapy treatment. This is usually given on an outpatient basis, with the patient returning perhaps every day until treatment is complete. To collect sufficient expertise and cutting edge equipment to optimally treat patients with life-threatening tumours is expensive. Oncology centres are therefore extremely busy and to maintain patient throughput must be able to plan a patient's treatment within a short time such as one hour. The planning process may involve several iterations as the physicist views the dose distribution and changes some beam parameters to improve the dose distribution.

There are various methods currently used to model radiation beams. One of the simplest of these is currently in use in many Oncology Centres—the Milan-Bentley method. It is popular as it functions well on relatively cheap equipment and is fast running. Forty-seven measurements are taken at 5 depths for each beam field width, depth, energy etc. along so called fan lines within the beam. These data are then stored and recalled when an appropriate treatment plan is devised.

Alternatively a broad radiation beam may be simulated by summing contributions from elemental pencil beams. Each pencil beam is considered to be composed of mono-energetic electrons having an angular divergence (mean angle) and a spread in angles about the mean angle that may be determined using Ferni-Eyges theory. Isodose curves may be found by integrating at different depths in the patient.

A further prior art method is to use a numerical method such as Monte Carlo modelling to obtain beam characteristics. Such simulations are performed separately to dose calculations, so that time requirements are not important. During the treatment planning process the effect of beam blocking and patient outline are simulated separately, using empirical or calculated methods.

Monte Carlo modelling is a statistical method that calculates the dose deposited in the region as a whole by simulating the passage of each photon through the region of interest. A typical passage of one incident particle, a photon, through a volume, divided into elemental volumes known as "voxels", is shown schematically in FIG. 3 of the accompanying drawings.

A gamma ray photon 80 is incident on a substance 90 made up of different media 100, 105, 110. The incident photon 80 enters the substance 90 and may undergo a variety of interactions. During the course of these interactions and through the production of electrons 85 energy is deposited into the substance 90. In a Compton scatter interaction 120 the incident photon 80 collides with an electron 85 and imparts energy to the electron 85. As a result the incident photon 80 loses energy and changes its direction. It may then undergo a pair production interaction 150. In this case a position 86 and an electron 85 are produced. The positron will quickly combine with an electron and undergo annihilation 160 in a puff of gamma rays 87. Alternatively the photon 87 may undergo a photoelectric interaction 140 in which it imparts all of its energy to an electron 85. The incident photon 80 thus loses its energy in a few, large interactions 120, 150, 160. Electrons 85 which have been ionised by the incident photon 80 undergo very many small interactions, depositing dose in the substance 90 throughout their path length. If an electron 85 has enough energy it may additionally undergo larger interactions to produce Bremsstrahlung radiation 130 or delta rays 89 ("delta rays" in this context are energetic electrons liberated from the target material by an interaction and which then have sufficient energy to produce further ionisations or excitations in the target material).

The incidence of these interactions varies as a complex function of the energy of the incident photon beam 45 and the atomic number of the interacting media 100, 105, 110. The type and number of interactions that do occur greatly influences the amount of energy deposited in different parts of the substance 90. As the beam 45 encounters multiple substances 90 on the way to the patient 10 it becomes difficult to predict how its cross section may be affected by scattered electrons 85, 89 and photon 87, from these interactions. There are, in theory, at least three ways of predicting the amount of energy thus deposited: empirical—by measuring the characteristics of the radiation beam 45; analytical—by making good physical assumptions about the behaviour of the beam 45 as it encounters different obstacles; and statistical/numerical—wherein the probability of the various interactions for one photon 80 is estimated and the paths of many millions of photons 80 and their interaction products 85, 86, 87, 89 are simulated.

Prior art solutions for radiotherapy treatment planning have focused on the empirical option, but the statistical/numerical option is more accurate and frequently used in radiation beam modelling. The computer run time of this option has prevented it being used routinely in radiotherapy treatment planning. The analytical option is generally too complex to set up for individual patients.

In a typical statistical/numerical simulation, such as Monte Carlo modelling, the probability of an interaction in each voxel is calculated by the simulation based on the energy of the particle and the material characteristics in the voxel. If an interaction takes place the simulation can calculate the probability of a particular type of interaction occurring and the probability that a particular amount of energy would be deposited in that interaction. These are then determined randomly for a particular particle. By simulating the passage of many millions of particles a dose distribution may be built up, with a variance dependent on the number of particles used.

Researchers in the high-energy physics community have developed computer programs such as EGS4 which have been used for many years to predict physical phenomena in large particle physics experiments. More recently PRESTA code has been developed which adapts EGS4 to the mega-volt particle energy range. Similar codes have been used in other application areas such as radiological medicine, industrial radiation hazards etc. Monte Carlo simulation methods provide an excellent representation of the physical processes involved and are particularly advantageous when predicting the interaction of radiation with inhomogeneous materials.

Unfortunately Monte Carlo modelling is computationally very expensive. The run time of the simulation is proportional to the number of incident particles simulated and the statistical variance is proportional to this number. The error, defined as the ratio between the statistical uncertainty in dosage and the value of the dosage, is inversely proportional to the square root of the number of particles. Therefore in order to reduce the error by a factor of 2, 4 times as many particles are needed, increasing run times by a factor of 4. However the error also depends on the number of interactions within each voxel, so that as the resolution is increased the computation time must increase with the inverse of the voxel volume to obtain the same statistical accuracy. Thus the computational cost of the method grows as $1/d^3$, where d is the size of the voxel. Current Monte-Carlo run times on affordable computers make the method totally impractical at resolutions needed for radiotherapy treatment planning. It is therefore necessary to introduce other variance reduction methods.

One such prior art variance reduction method is to use a large number of particles in a volume of interest, and a much smaller number in the rest of the volume. This may be achieved by replicating particles as they enter the volume of interest and discarding some particles as they leave this region with a probability chosen to balance the initial replication factor.

Within the region of interest, all the replica particles are allowed to proceed independently, effectively boosting the statistical accuracy of the simulation within this region. However, because only a fraction of these particles have to be tracked before and after the region of interest this improvement is achieved at lower computational cost than would be needed without particle splitting.

Normally, particle splitting is exploited by simulating the treatment head using a very large number of particles, to obtain an accurate characterisation of the radiation beam in terms of the distribution of particle types, position, direction and energy. This distribution is then sampled to provide incident particles for a separate simulation of individual patient treatments, removing the need to track all these particles all the way from the treatment system.

Unfortunately using affordable hardware this is still not sufficient to enable Monte Carlo modelling methods to be used in radiotherapy treatment planning. Furthermore it does not address the problem of vastly increasing run-times at increasing spatial resolution.

WO90/14129 discloses a radiation modelling system which notes the high computational cost of dosage calculation at high resolution, and proposes using high resolution (e.g. 1 mm) close to a region of interest and low resolution (e.g. 5 mm) elsewhere.

WO91/18552 discloses the use of diagnostic machines to capture individual patient characteristics and to use these with a convolution algorithm to predict dosage.

U.S. Pat. No. 5,341,292 proposes constructing a fully three dimensional but low resolution model of dosage using Monte Carlo techniques. A coarse-grained definition of tissues is obtained by averaging high-resolution anatomical data from a diagnostic scanner.

WO97/42522 proposes the use of a parallel computing platform to carry out Monte Carlo dosage calculations. The parallel computer uses a hybrid between shared and distributed memory.

This invention provides a radiation modelling apparatus comprising:
a stochastic modelling kernel operable to receive parameters of an irradiation, data representing a radiation source and data representing material properties of a medium to widergo the irradiation and to calculate a distribution of radiation energy or dosage resulting from the irradiation;
characterised by a filter arranged so as to remove components comprising substantially statistical noise from the output of the modelling kernel.

Viewed from another aspect this invention provides a method of calculating energy or dosage deposited from a radiation beam comprising the steps of:
executing a stochastic simulation on a computing means to determine the amount of energy or dosage deposited in a substance as a result of a radiation beam incident on the substance;
characterised by filtering the output of the stochastic simulation to remove components, comprising substantially statistical noise.

The skilled man will understand that the filter may be applied to the distribution of energy, or derived distributions of radiation dosage or biological activity etc. produced from the modelling kernel.

This invention is particularly, though not exclusively, applicable to radiation modelling using a Monte Carlo kernel. In this case the use of a filter provides a reduction in statistical error, independently of variance reduction methods such as particle splitting which may also be introduced into the Monte Carlo modelling kernel.

This invention recognises that the statistical methods used in Monte Carlo modelling mean that the process is a random or stochastic process. Although each particle has a probability of interacting in a voxel which may be influenced by, for example, the density of the medium in that voxel, the simulation determines whether an interaction takes place entirely randomly. If, therefore, only 10 particles are simulated there is a high probability that the resultant energy distribution will not resemble the result when a different 10 particles are simulated. However many particles are simulated the results will be slightly different i.e. the dose distribution image will be overlain with random noise.

The random nature of this process is similar to many scientific experiments. Data from these experiments is commonly slowly varying and overlain with random noise. Data from a Monte Carlo "experiment" in radiotherapy treatment planning also tends to be slowly varying, as the tissues in the body do not vary greatly in density compared, for example, to lead and air. Furthermore in a Monte Carlo model each particle is simulated as a separate entity. The noise in each voxel will therefore be independent.

Data smoothing is applied to the results of scientific experiments to allow the eye to follow the results more easily, or as a means of making estimates from the parameters of a graph. The central premise of data smoothing is that the variable measured is slowly varying and overlain with random noise. It can then be useful to replace each data point by some local average of surrounding data points. Since nearby points measure very nearly the same underlying value, averaging can reduce the level of noise without greatly biasing the value obtained.

An effective high resolution simulation can thus be constructed by feeding output from a physically accurate Monte Carlo simulation into a low-pass digital filter module. The filter may be of many different types but preferably is a Savitsky-Golay or similar type of filter in which smoothing may be accomplished with minimal loss of resolution This type of filter assumes that distant data points have significant redundancy such that the underlying function should be locally well fitted by a polynomial. This is generally true for the dose distribution resulting from a Monte Carlo or similar simulation as the physical processes involved have a well defined length of action. For example the range of a 1 MeV electron in water is 4.2 mm. Thus beyond this range the data points will be completely redundant.

The physical range of the simulated particles is only dependent upon their initial energy and the characteristics of the media with which they interact and do not change whatever the voxel resolution available to the user. This means that the effect of filtering may be increased for high resolution data, overcoming the problem of increased simulation times for this data. As resolution is improved, and adjacent dosage values move closer together, statistical correlation becomes stronger, enabling more ambitious filtering to be used. For example each voxel encloses a volume of 2 $mm^3$ (the current state of the art). To cover the physical range of the a 1 MeV electron a 3 point filter must be constructed. If the voxel resolution improves to 0.2 $mm^3$ the computational cost would increase by a factor of 1000.

However a 21 point filter may now be constructed to cover the physical range of the particle, thus increasing the effectiveness of filtering, and at least partly offsetting the increase in computational cost at higher resolutions.

In preferred embodiments where the simulation output comprises a voxel map or other sampled spatial representation, the filter may be arranged to remove certain high frequency components from this sampled signal.

Embodiments of this invention advantageously combine filtering with particle splitting and/or other variance reduction methods to further improve the results.

Embodiments of the invention will now be described, by way of illustration only, with reference to the accompanying drawings, throughout which parts are referred to by like references and in which:

FIG. 1A schematically shows a cross section through a head of a patient receiving radiotherapy treatment.

FIG. 1B schematically shows the head cross section in more detail, including details of the isodose contours from the treatment received.

FIG. 2 schematically shows a typical relationship between dose and normal tissue injury and tumour cure;

FIG. 3 shows schematically a path of a photon through a substance and its interactions with said substance;

FIG. 4 schematically shows an embodiment of the invention incorporated into a radiotherapy treatment centre;

FIG. 5 shows schematically a radiotherapy planning computer in greater detail;

FIG. 6 schematically shows the operation of a typical prior art radiotherapy planning system;

FIG. 7 schematically shows the operation of the embodiment of FIG. 4;

Figure 5:
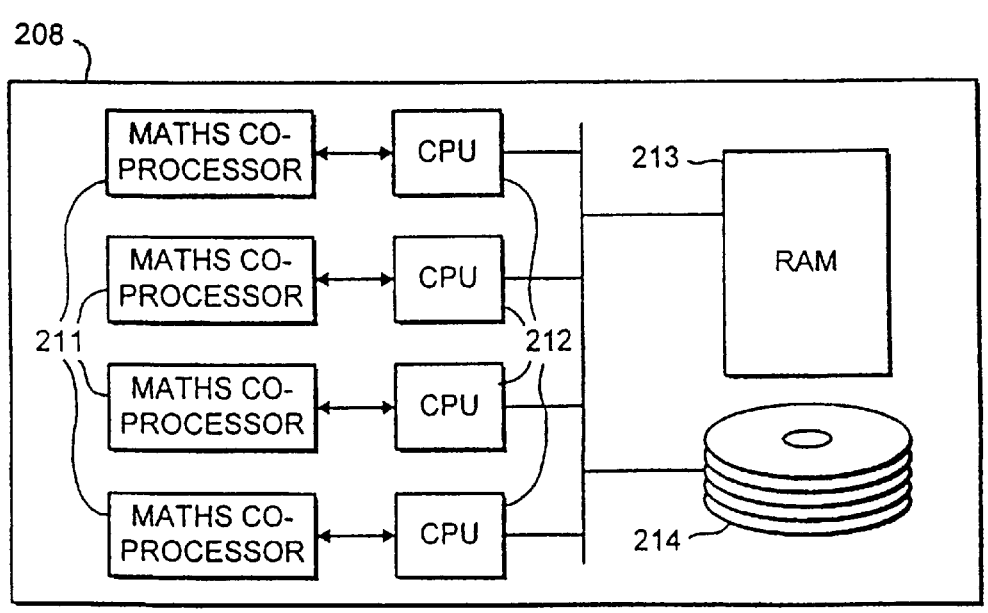
Figure 11A:
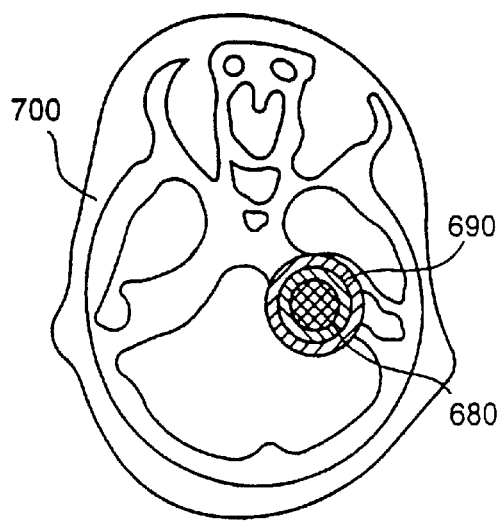
Figure 11B:
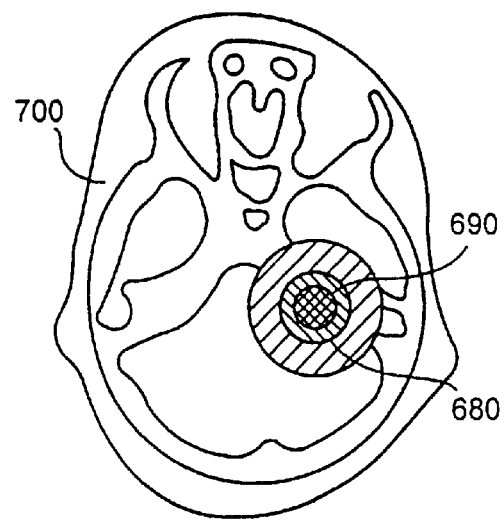
Figure 12:
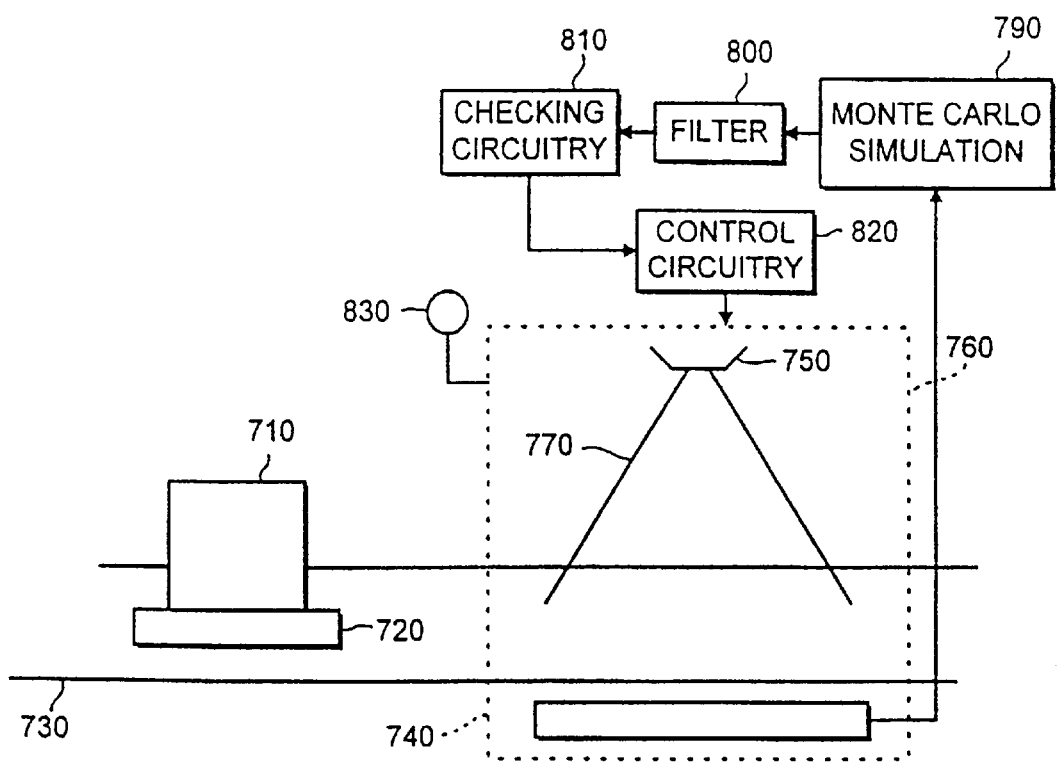

FIG. 11A schematically shows results from a revised treatment plan implemented on the prior art system;

FIG. 11B shows schematically results from the same revised treatment plan implemented on the embodiment of FIG. 5; and FIG. 12 shows another embodiment of the invention in a sterilising device.

Figure 1A:
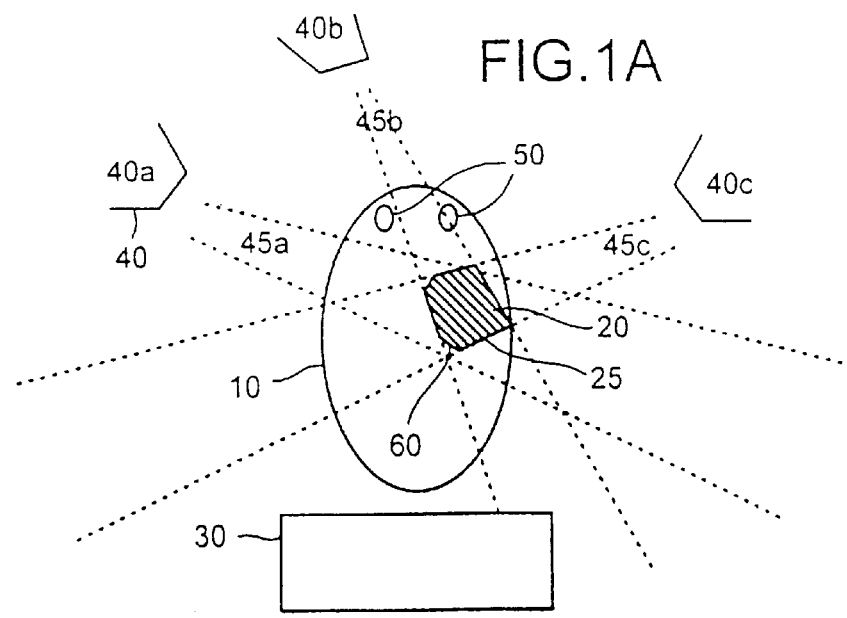
Figure 1B:
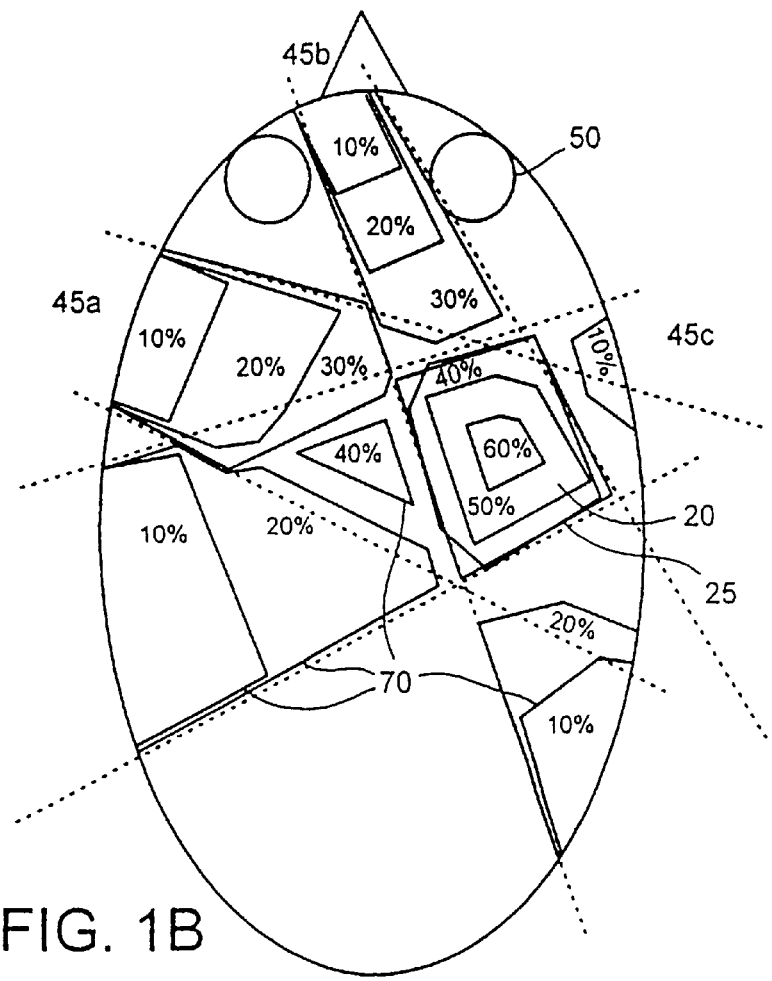
Figure 2:
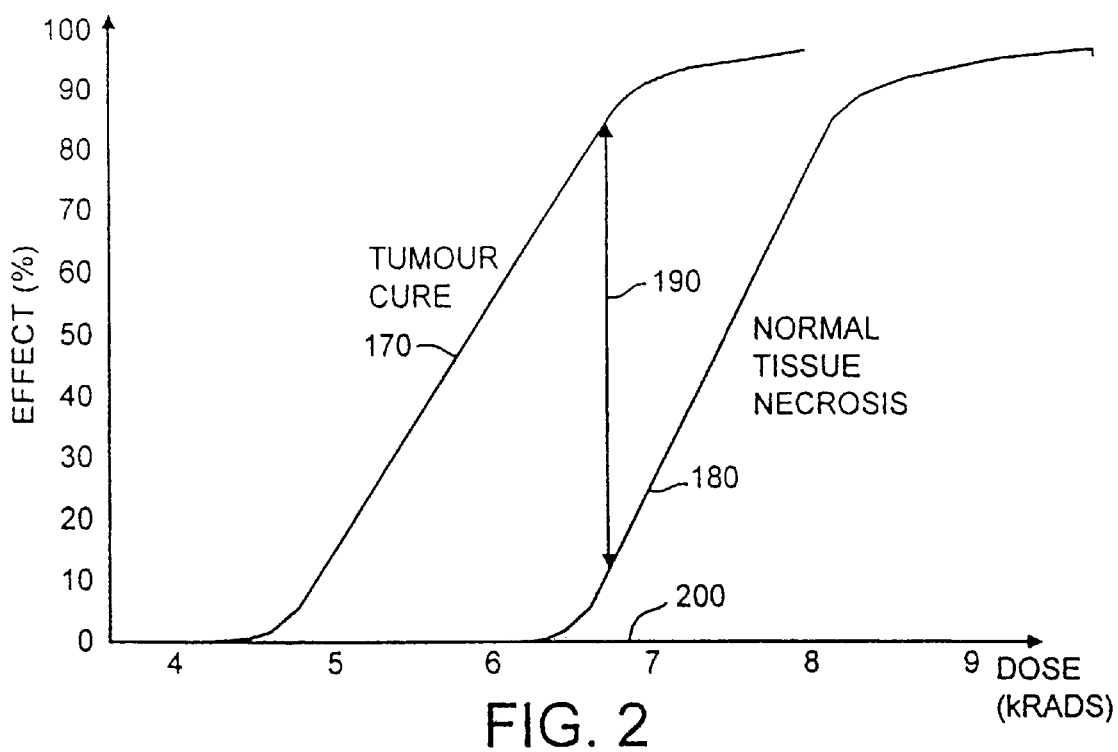
Figure 3:
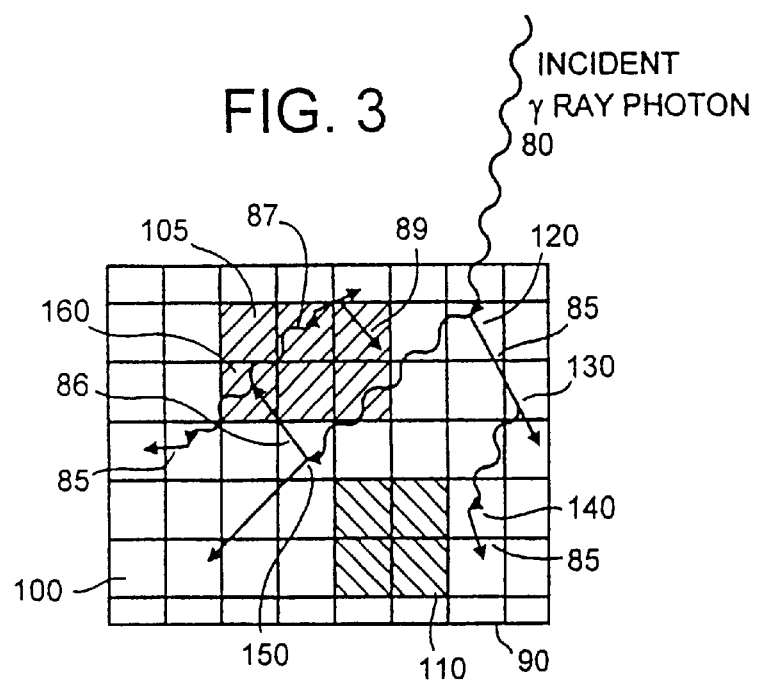
Figure 4:
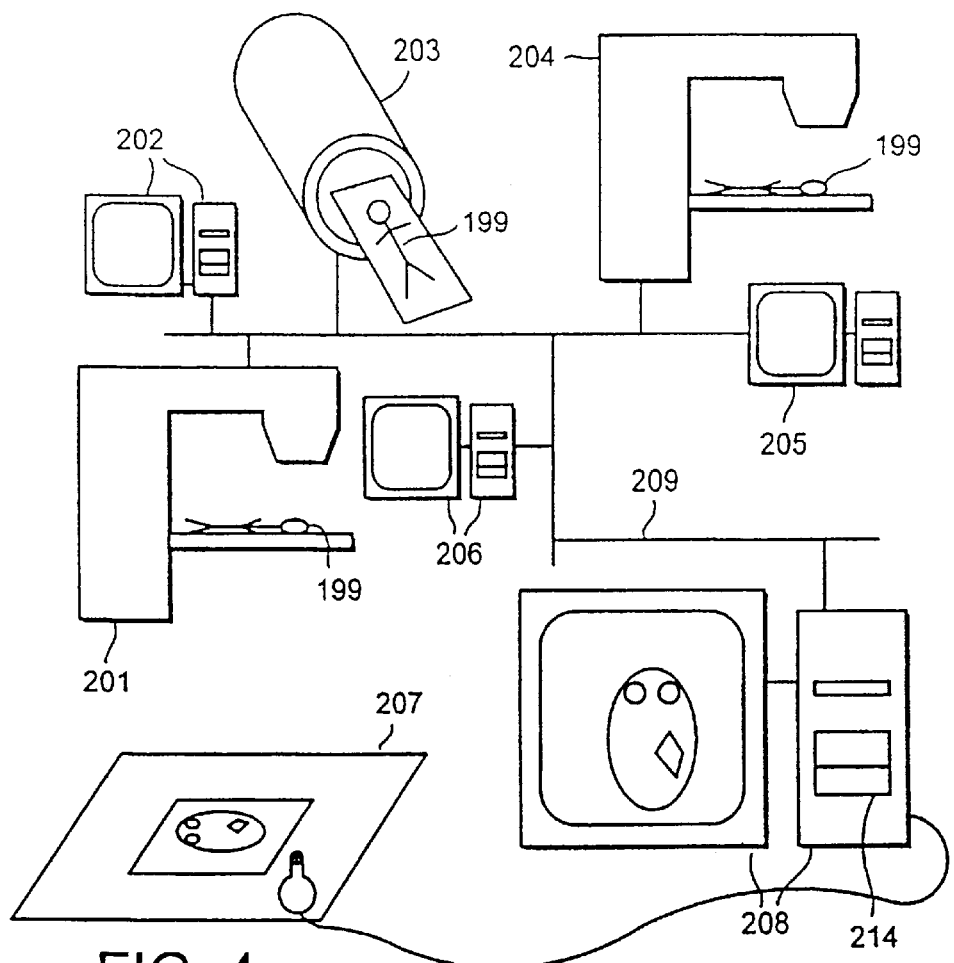

In FIG. 4 a networked radiotherapy treatment centre is schematically shown. A network 209 connects a computed tomographic (CT) scanner 203, a radiotherapy treatment simulator 204 and a radiotherapy treatment machine 201, together with their associated computer controllers 202, 205, 206. A radiotherapy treatment planning computer 203, on which a Monte Carlo kernel 340 runs is also connected to the network 209. The radiotherapy planning computer 208 may draw data from the CT scanner 203 concerning the outline and density of a patient 199, or such information may be entered directly into the radiotherapy planning computer 208 using a digitiser 207. A physicist then uses a user interface 240 to set up a treatment plan, deciding where radiotherapy beams should be placed, their shape and evaluating whether any beam blocking is required. The radiotherapy planning computer 208 uses this information, together with stored beam property and patient tissue data to generate a treatment plan. This process is described in more detail later. Radiographers then examine the plan on the treatment simulator controller 205 and set-up the patient 199 as indicated by the treatment plan on the treatment simulator 204. X-rays are taken to verify that included and excluded tissues are exactly as required. The patient 199 marked to make set-up on the radiotherapy treatment machine 201 easier. If the treatment plan is satisfactory the patient may now proceed to be treated on the treatment machine 201.

FIG. 5 schematically shows the radiotherapy planning computer 208 in more detail. Several central processing units 212 run a modelling kernel 340 and a low pass filter 370, whose operation is described further below. Maths co-processors 211 speed up the operation of the central processing units 212 and data may be stored at run-time on random access memory 213 or more permanently in optical disk storage unit 214.

Figure 6:
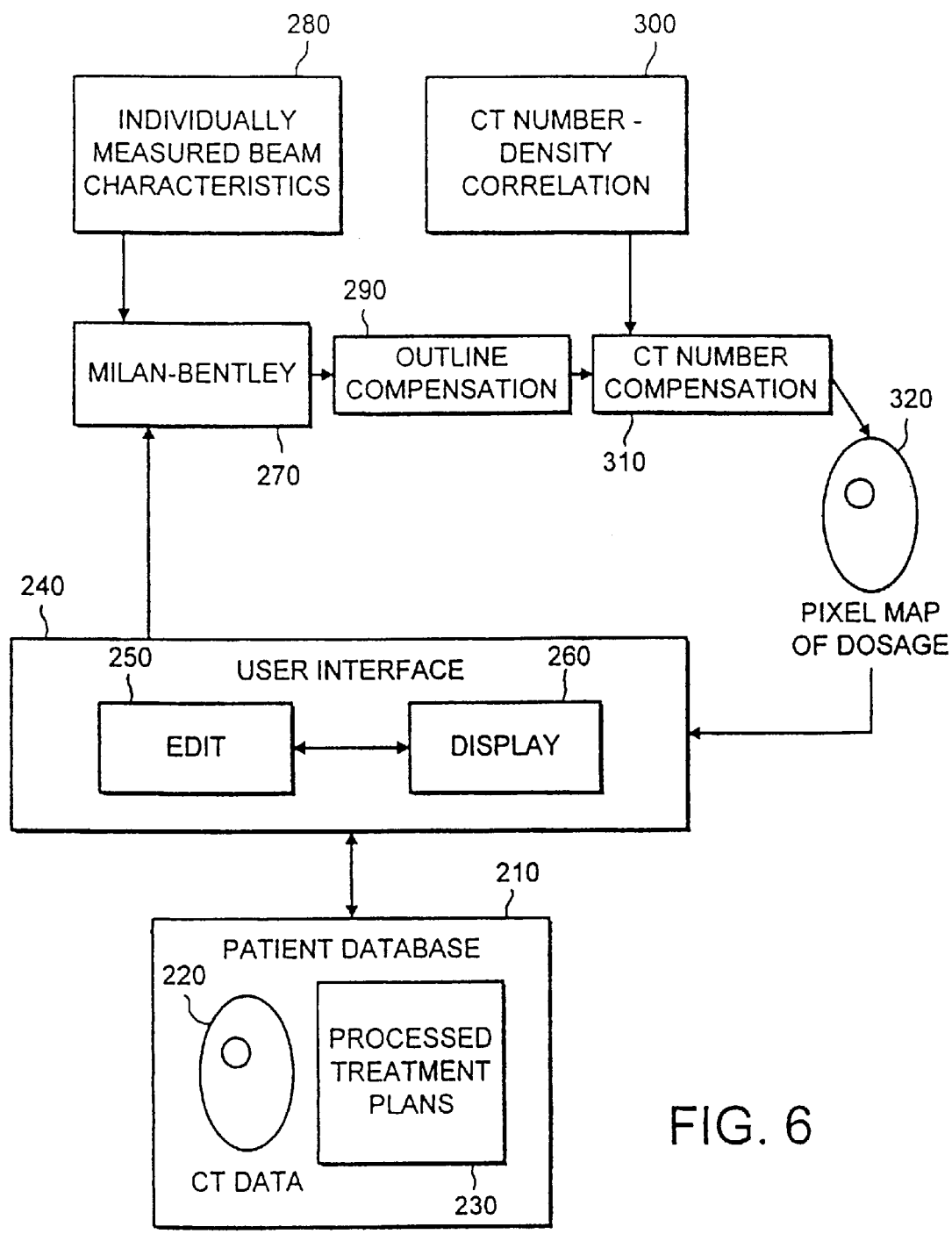

The operation of a typical prior art radiotherapy planning system is shown in FIG. 6. A patient database 210 stores details of patients previously treated, containing computed tomographic (CT) data 220 showing cross sections of tumour site and any treatment plans 230 which were evaluated for this patient. The data in this catabase 210 may be called up by a user interface 240 so that for a new patient the CT data 220 may be displayed by a display 260 which is typically large (for example 17 inches) and of good quality (for example 1240×1024 pixels).

The user interface 240 also has an editing program 250 which enables a treatment plan to be set-up on the CT data, containing information concerning the number of radiotherapy beams 45, their distance from the patient 10, their relative weighting and the presence of any beam shaping devices. Once the plan is set-up isodose lines 70 are calculated using an empirical model, typically the Milan-Bentley model 270. Essentially this model 270 relies on measurements, originally made in a large water tank on commissioning of the equipment, for many different field sizes and beam shaping devices. Measurements are made of the dose deposited in this tank along 47 "fan lines" and five "profile lines" for each size of beam. An array of dosage points 280 is thus created for many practically used beams, and for field sizes in-between those held in this database 280 extrapolation may be used.

The output from the Milan-Bentley model 270 consists of a basic set of isodose curves 70 for the water tank. It is thus necessary to modify these to take account of patient shape using an outline compensation algorithm 290. Finally the different densities of tissue are accounted for by looking up the appropriate CT number—density correlation in a look-up table 300 and applied by a CT number compensation algorithm 310.

Both the outline compensation algorithm 290 and the CT number compensation algorithm 310 typically work by altering the effective distance between the source of the radiation and the point of interest. Thus a dense material such as bone will be moved toward the source of radiation for the purposes of dose calculation while a less dense material such as lung will be effectively moved away from the source of radiation. It is thus impossible for these algorithms to compensate for, for example the effect of interfaces between different media or for the effect of a neighbouring change in the patient outline on a particular point. The compensation algorithms 290, 310 are thus no more than useful approximations.

The output from the CT number compensation algorithm 310 is generally in the form of a pixel map 320 of the dosage deposited in the patient but it is possible to produce a series of pixel maps at different slice heights to give the impression of the three dimensional dosage. The dosage map 320 is then displayed on the user interface 240 and evaluated by a planner for conformance with clinical objectives. As a result the beam parameters may be altered and the planning process iterated until a near optimal plan is arrived at.

Figure 7:
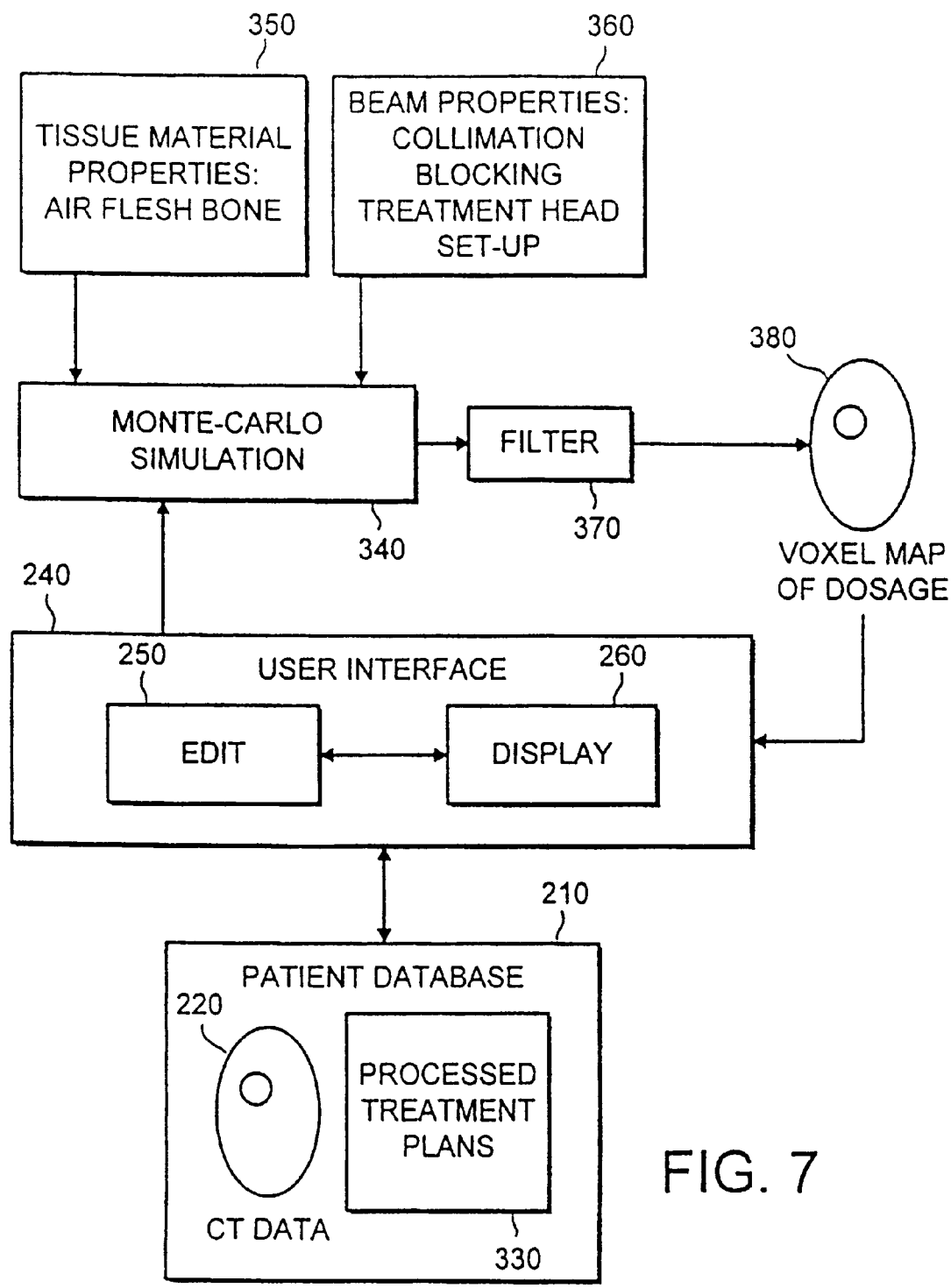

FIG. 7 shows schematically the operation of the embodiment of FIG. 4. The patient database 210 and the user interface 240 are substantially the same as in the prior art system, although a processed treatment plan 330 comprises treatment parameters together with a voxel map 380 of the dose distribution. From the user's point of view, therefore the two systems are very similar. Once the treatment parameters have been set by the user the energy or dosage deposited in each voxel is calculated by a Monte Carlo simulation kernel 340. This kernel 340 uses pre-processed data 350 concerning the material properties of typical patient tissue and pre-processed data 360 concerning the effect of collimation and treatment head set-up on the beam. This data is analogous to the empirical data 280 stored in the prior art system shown in FIG. 4, but may be calculated rather than measured. The Monte Carlo simulation 340 proceeds until it reaches a pre-set statistical variance.

The output from the Monte Carlo simulation 340 is passed to a low pass digital filter 370. After a short run-time the statistical uncertainty in the simulation data output from the Monte Carlo simulation 340 will be large, but since the error at each voxel will be independent, filtering can be used to suppress the uncertainty at all points in the three-dimensional data set. To compensate for increased resolution the filter 370 has a variable aperture which may be tuned to the length scale required for each voxel. Varying this aperture increases the effectiveness of filtering for high resolution data, at least partly offsetting the otherwise large increase in computation time needed.

The filter 370 output consists of a voxel map of the dosage 380 which may then be displayed by the display 260 in the user interface 240. The planner may then consider whether the plan meets clinical objectives and re-iterate the planning process as necessary.

Figure 8:
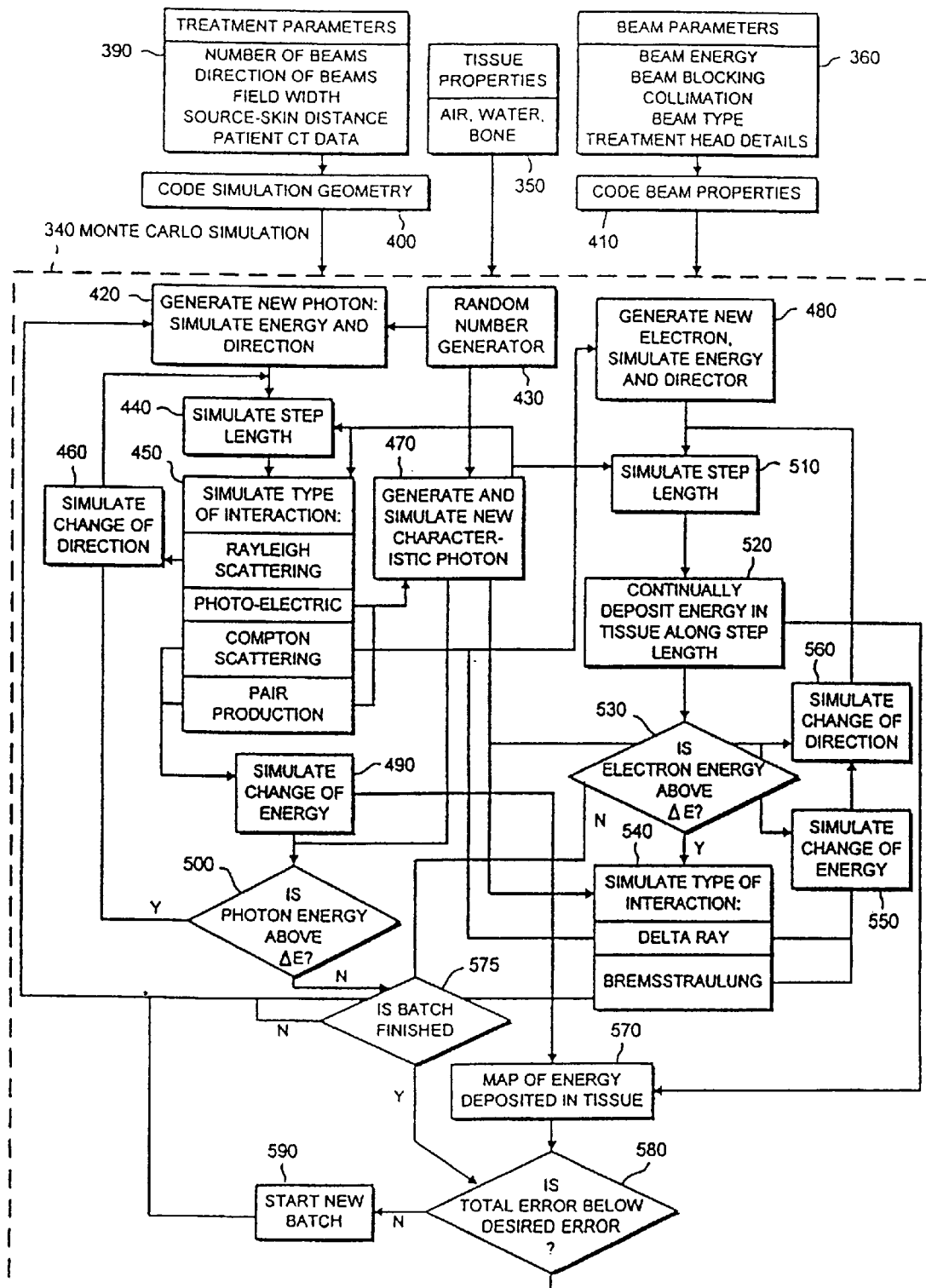
FIG. 8 shows schematically the operation of a Monte Carlo kernel in more detail.

FIG. 8 shows the operation of a typical Monte Carlo simulation in more detail. Information such as treatment parameters 390, tissue properties 350 and beam parameters 350 is input into the simulation kernel. This information may be pre-processed such as in the case of the tissue properties 350, or, as in the case of the treatment parameters 390 require coding in a step 400. The step 400 translates the simulation geometry into a form suitable for use by the Monte Carlo kernel 340, while a different step 410 completes a similar procedure for the beam properties 360.

The Monte Carlo simulation 340 continually generates and simulates the life of different incident particles, in this case photons, whilst the variance of the energy deposited in the image remains above a user-set threshold. The general procedure is to draw up a probability function depending on beam and patient properties and to determine randomly which of a particular event occurs. Firstly in a step 420 the kernel 340 generates a new photon. This requires simulation of the new photon's energy and direction, given the beam parameters 360. Information from beam parameter coding step 410 is used to set up a probability function which determines the likelihood of the photon possessing a particular value for energy or direction. This particular value for the photon is simulated by using a random number generator 430. This random number generator 430 is a vital part of the simulation and needs to be of very high quality. Known and appropriately tested random number generators are suitable.

Once a new photon is generated the length of space that it transverses before undergoing an interaction is simulated in a simulation step 440. This will depend on the treatment parameters 390, and the tissue properties 350. Next the type of interaction undergone by the photon is simulated in a simulation step 450. The probability function for different types of interaction will depend on the individual photon 80 properties and the material properties of the medium 100, 105, 110 in which the interaction occurs.

The next step in the simulation will depend on the type of interaction undergone. For example, for classical (or Rayleigh) scattering there is no change in the energy of the photon and the Monte Carlo kernel moves on a simulation step 460 to simulate the change of direction of the photon before returning to the previous step 440 to simulate the step length before a further interaction. For a photoelectric interaction, Compton or pair production interaction energy is deposited into the tissue and the kernel records this in a map of the energy deposited in the tissue 570. Additionally an electron is generated in step 480 with energy and direction properties which are physically determined by the type of interaction that generated the electron.

For pair production and Compton interactions a change in energy of the photon must also be simulated in a step 490. If the photon energy is sufficient for another interaction to take place (i.e. the photon has not been absorbed) the change in direction is simulated in the change of direction step 460, the probability function of which will again depend on the type of interaction occurring. If a photo-electric interaction occurs a characteristic photon must be generated in a simulation step 470 which if its energy is found to be sufficient in another step 500 may interact further in its turn.

Electrons 85 generated by the Compton 120, pair production 150 or photo-electric 140 processes are simulated in a further step 480. Their energy and direction probability functions will be calculated by the type of interaction and the properties of the parent photon 80 and randomly simulated. The step length until a large interaction involving the electron is then simulated in another step 510. Small interactions, which take place along the entire length of the step length, are simplified to a continual constant deposition of energy and simulated in an energy deposition simulation step 520 which transmits that data to the map of the total energy or dosage deposited in the tissue 570.

In a following step 530 the energy of the electron is evaluated. It may have run out of energy before a large interaction occurs, in which case its simulated life is over and the algorithm moves to an evaluation step 575. If there is sufficient energy for a large interaction to occur the type of interaction is randomly determined in another simulation step 540. If a delta ray 89 results, another electron 85 is generated in a following step 480 while if Bremsstrahlung radiation 130 occurs another photon is generated in the first simulation step 420. In either case the change in energy of the electron 85 simulated in a following simulation step 550 and the change in direction of the electron 85 in a further step 560. The probability functions shaping the results from these steps are determined by the original electron properties and whether a delta ray was produced or Bremsstrahlung radiation occurred.

Once the original incident photon and all interaction products have been fully simulated such that their energy has dissipated, another incident photon is generated in the simulation step 420. Normally a minimum number of photons are generated, and divided into five or ten equal batches. At the end of each batch, evaluated in a simulation step 575, the mean and standard deviation amongst all the batches is calculated and used to calculate the statistical error of the overall result in a simulation step 580. If he error is too high, a further batch is started in a simulation step 590 and the process is repeated until a desired error is reached. If not, the simulation is considered to be finished and the map of the energy or dosage deposited in the tissue 570 is passed to the filter means 370.

Figure 9:
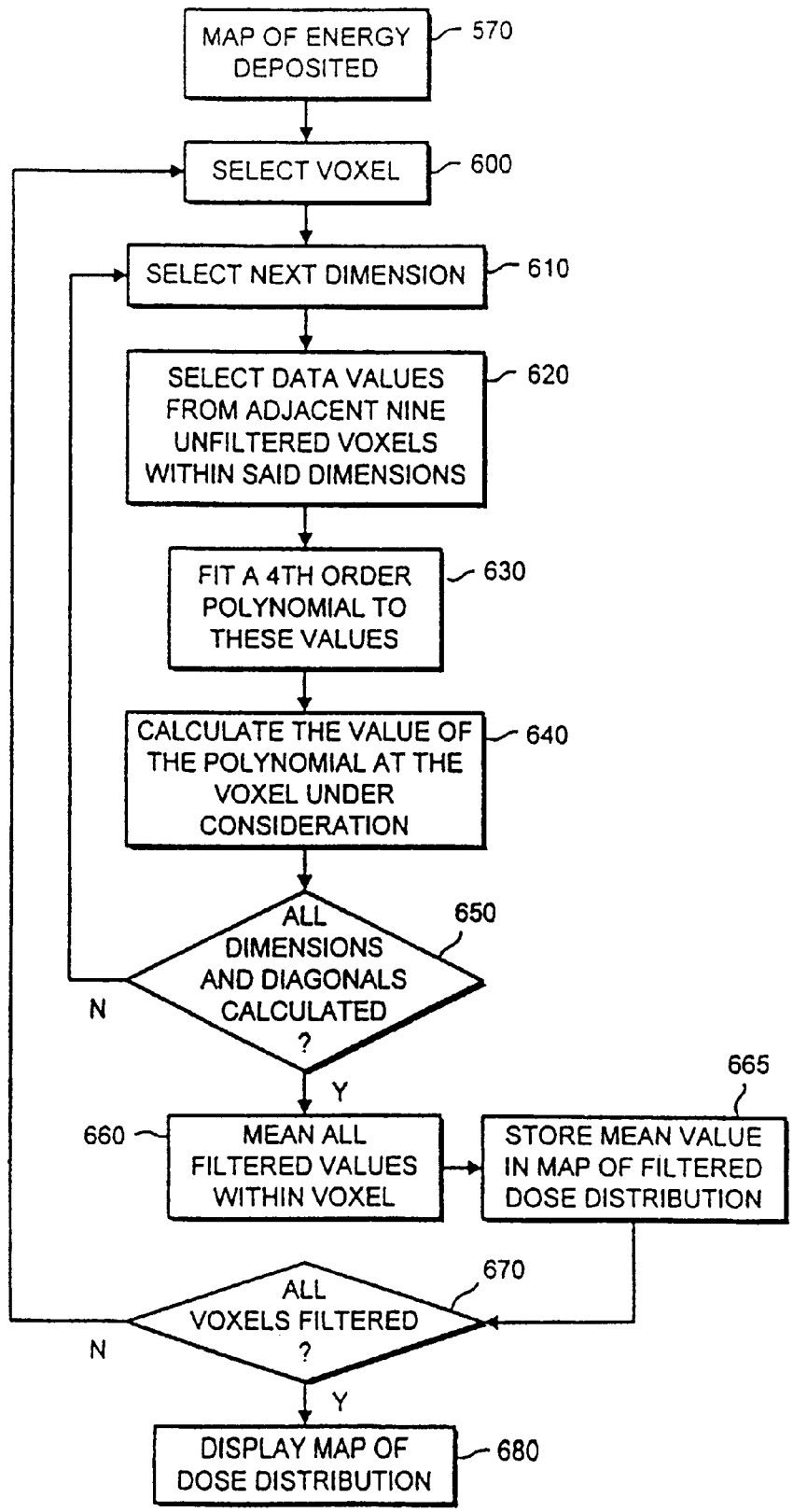
FIG. 9 shows schematically the operation of the embodiment of FIG. 4 in more detail.

The detailed operation of the digital filter 370 is shown schematically in FIG. 9. The filter selects one voxel of the energy or dosage map in a step 600, each voxel being represented by a Monte Carlo simulated energy data point. One dimension of the map 570 is selected in a second step 610. The nine unfiltered values for the nine adjacent data points to the selected voxel along the selected dimension are then retrieved from the map 570 in a third step 620, and in a fourth step 630 a 4th order polynomial is fitted to these values. In a calculation step 640 the value of the polynomial at the selected voxel is calculated. These steps are then repeated for each dimension and for diagonals between dimensions. After an evaluation step 650, therefore 7 values representing the results from these polynomials are available. The mean of these is taken in an averaging step 660 and recorded in a map of the filtered dose distribution 680 in a simulation step 665. This process is repeated for all voxels, and when all voxels have been filtered, as determined by a step 670, the map of the filtered dose distribution is displayed in a step 680.

This type of filtering may be referred to as so-called "Savitsky-Golay" filtering, as described in the reference, "Numerical Recipes in FORTRAN: The Art of Scientific Computing", Cambridge University Press, 1992.

Figure 10A:
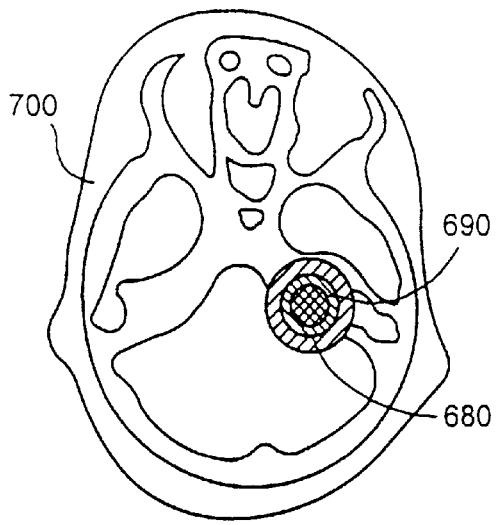
FIG. 10A shows schematically typical results from a prior art system.
Figure 10B:
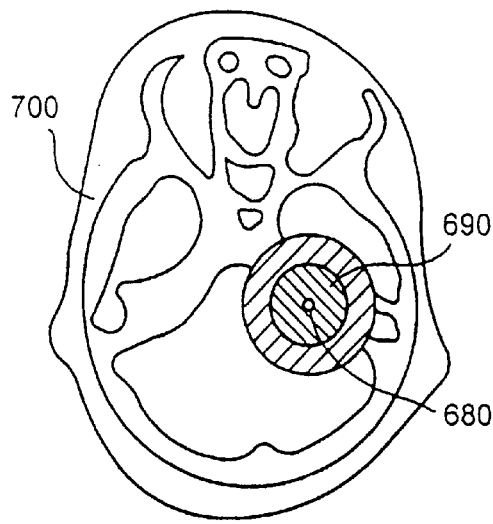
FIG. 10B shows schematically results for the same treatment plan parameters for the embodiment of FIG. 5.

FIG. 10 schematically illustrates two isodose distributions, overlaid on CT images, that have been generated by a prior art system (FIG. 10A) and by the embodiment of FIG. 4 (FIG. 10B). In these images a tumour 680 lies behind a bony region 690 inside a patient's head 700. The isodose distribution in FIG. 10A shows the tumour 680 receiving a uniformly high dose, so this treatment plan would be accepted as meeting clinical objectives. The isodose distribution generated by the present embodiment, however, shows that the tumour 680 is underdosed due to screening by and scattering from adjacent bony region 690. This treatment plan would therefore not meet clinical objectives and, if carried out, it is unlikely that the treatment would be successful. This cannot be determined using the prior art system. The under-dosing is only shown with the greater accuracy available from the present embodiment.

FIG. 11 shows the isodose distribution from a revised treatment plan, with different beam weighting and orientation to the treatment plan of FIG. 10. The results from the prior art system are shown in FIG. 11A and the results from the present embodiment is shown in FIG. 11B. The results in FIG. 11B show much better coverage of the diseased tissue, indicating that this treatment would be more likely to be successful. The results shown in FIG. 11A for the prior art system are clinically indistinguishable from the results in FIG. 10A, thus the prior art system would inaccurately indicate that there is no difference between the two plans. The present embodiment is clearly superior to the prior art system.

FIG. 12 shows another embodiment of the present invention as part of a steriliser, operable to sterilise foodstuffs or medical items. A container 710, with a volume which may be varied by changeovers and other factors upstream in a manufacturing process, is packaged and carried on a conveyor belt 730 by a pallet 720. This container is sterilised by an x-ray beam 770, derived from a rotatable x-ray head 750 in order, for example, to kill bacteria and elongate the shelf life of a foodstuff.

To attain good standards of food or medical safety and hygiene using this method the whole volume within the container 710 must be irradiated past a threshold value. Excess radiation, however could cause the contents itself to degrade. It is therefore important that a reasonable uniformity of irradiation, past a threshold value, is attained throughout the container 710. Modern factories, however, require flexible operations so that changing over to different products (which may have different densities and therefore require different irradiation times) may be simply and speedily accomplished. In this instance the steriliser 760 is sited substantially at the end of the production process before the pallets 720 are loaded onto lorries. A sufficient uniform dose must be received by each container 710 whatever its volume. To maintain throughput, however, the sterilisation process must be accomplished within a reasonable time.

When a pallet arrives at the steriliser 760, which comprises a closed box screened with lead the x-ray head 750, set at a field size sufficient to irradiate the largest possible container 710, first gives a brief burst of x-rays 770. Some of these are attenuated by the contents within the container 710 and the flux that arrives at electronic sensors 740 provides an indication of the density of the contents of the container. The x-ray head 750 and the electronic sensors 740 are connected and mounted on a rotatable gantry so that the container 710 may be x-rayed from different angles.

The output from electronic sensors 740 forms the input to a Monte-Carlo simulation 790 substantially similar to the one detailed in FIG. 8. The output from this simulation is filtered by a filter 800 substantially similar to the one detailed in FIG. 9. The uniformity of the output is then examined by checking circuitry 810, and if the dose received by the whole of the container 710 lies between two values (determined by the particular composition of the contents, which may be stored as part of the manufacturing process control system) the x-ray head 750 gives a longer burst of x-rays 770 in order to sterilise the container 710. If the uniformity is not sufficient the control circuitry 820 may alter the angle of the x-ray head, or try a combination of different angles, and re-iterate the process. If the attenuation is greatly non-uniform an alarm 830 will be sounded, and an alert message appear on the manufacturing control system to alert an operator to the problem. This system, therefore, may detect foreign bodies or a lower than expected volume in container 710 as well as ensuring that the sterilisation process proceeds effectively and quickly.

What is claimed is:

1. A radiation modeling apparatus for providing simulation data of a desired resolution, comprising:
   a stochastic modeling kernel operable to receive parameters of an irradiation, data representing a radiation source and data representing material properties of a medium to undergo the irradiation and to calculate a distribution of radiation energy or dosage resulting from the irradiation, a physical process associated with interaction between the irradiation and the medium having a defined length of action; and
   a filter having a length scale comparable to the length of action and arranged so as to remove components comprising substantially statistical noise from the output of the modeling kernel so as to reduce computation time required to produce simulation data of the desired resolution.

2. Apparatus according to claim 1, wherein the stochastic modeling kernel is operable to simulate the interactions of individual incident radiation particles with the medium.

3. Apparatus according to claim 2 wherein the particles are photons.

4. Apparatus according to claim 3 wherein the photons are in the Megavolt energy range.

5. Apparatus according to claim 1 wherein the simulation is operable to simulate a radiation distribution in three spatial dimensions.

6. Apparatus according to claim 1, in which the kernel is responsive to data representing a shape and material disposition of a substance undergoing irradiation.

7. Apparatus according to claim 6, wherein the data representing the shape and material disposition is derived by x-ray examination of the medium.

8. Apparatus according to claim 1, comprising an image assembler operable to assemble output from the simulation into an image representing energy deposited in different parts of the media.

9. Apparatus according to claim 1, comprising an editor operable to edit the manner in which a simulated radiation beam is directed upon the media undergoing irradiation and a display operable to display results to a user.

10. Apparatus according to claim 9 wherein the display is operable to display a voxel map of the energy deposited in the media.

11. Apparatus according to claim 1, wherein the filter is a low pass spatial filter.

12. Apparatus according to claim 1, wherein the filter has a variable aperture tunable to vary the length scale of the filter to increase the effectiveness of filtering.

13. Apparatus according to claim 1, wherein the filter is a Savitsky-Golay filter.

14. Apparatus according to claim 1, wherein the filter is a one dimensional filter, arranged to sequentially filter the output from the simulation kernel in successive spatial dimensions and to output the mean of these filtering operations.

15. Apparatus according claim 1, wherein the stochastic modeling kernel is a Monte Carlo type.

16. A radiotherapy treatment planning apparatus for providing simulation data, comprising:

a stochastic modeling kernel operable to receive parameters of an irradiation, data representing a radiation source and data representing material properties of a medium to undergo the irradiation and to calculate a distribution of radiation energy or dosage resulting from the irradiation, a physical process associated with interaction between the irradiation and the medium having a defined length of action;

a filter having a length scale comparable to the length of action and arranged so as to remove components comprising substantially statistical noise from the output of the modeling kernel so as to reduce computation time required to produce simulation data of the desired resolution; and a user interface operable to edit data input to the modeling kernel and display data output from the filter.

17. A radiotherapy treatment planning system according to claim 16, comprising a particle multiplier operable to increase the number of particles simulated in a region of interest of the medium.

18. A method of calculating energy or dosage deposited from a radiation beam comprising:

executing a stochastic simulation on a computing means to determine the amount of energy or dosage deposited in a substance as a result of a radiation beam incident on the substance; and filtering the output of the stochastic simulation to remove components, comprising substantially statistical noise, with the filtering having a length scale comparable to a length of action associated with a physical process occurring between the radiation beam and the substance.

* * * * *